United States Patent
Del Soldato et al.

(10) Patent No.: US 7,199,258 B2
(45) Date of Patent: Apr. 3, 2007

(54) PROCESS FOR PREPARING NITROOXYDERIVATIVES OF NAPROXEN

(75) Inventors: Piero Del Soldato, Milan (IT); Giancarlo Santus, Milan (IT); Francesca Benedini, Milan (IT)

(73) Assignee: Nicox S.A., Sophia Antipolis - Valbonne (FR)

(*) Notice: Subject to any disclaimer, the term of this patent is extended or adjusted under 35 U.S.C. 154(b) by 55 days.

(21) Appl. No.: 10/523,722

(22) PCT Filed: Aug. 6, 2003

(86) PCT No.: PCT/EP03/08698

§ 371 (c)(1),
(2), (4) Date: Sep. 14, 2005

(87) PCT Pub. No.: WO2004/020384

PCT Pub. Date: Mar. 11, 2004

(65) Prior Publication Data

US 2006/0173005 A1 Aug. 3, 2006

(30) Foreign Application Priority Data

Aug. 29, 2002 (IT) .............................. MI02A1861

(51) Int. Cl.
*C07C 203/04* (2006.01)
(52) U.S. Cl. .................................... 558/482
(58) Field of Classification Search ................ 558/482
See application file for complete search history.

(56) References Cited

U.S. PATENT DOCUMENTS 5,700,947 A * 12/1997 Soldato ....................... 548/491
6,700,011 B1 * 3/2004 Benedini et al. ............ 558/482
2005/0234123 A1* 10/2005 Belli et al. .................. 514/509

FOREIGN PATENT DOCUMENTS

| WO | 95/09831 | 4/1995 |
| WO | WO 95 09831 A | 4/1995 |
| WO | 98/25918 | 6/1998 |
| WO | WO 98 25918 A | 6/1998 |
| WO | 01/10814 A1 | 2/2001 |
| WO | WO 01 10814 A | 2/2001 |

OTHER PUBLICATIONS

Kawashima, et al.; "Synthesis and Pharmacological Evaluation of (Nitrooxy)alkyl Appovincaminates"; vol. 36, pp. 815-819; 1993.

Ogawa, et al.; "Synthesis and Antihypertensive Activites of New 1,4-Dihydropyridine Derivatives Containing Nitrooxyalkylester Moieties at the 3-And 5-Positions"; vol. 41, No. 6, Jun. 1993.

Derwent Publications Ltd.; Kawaken Fine Chem. Co. Ltd.; JP 05 279359 A; Oct. 26, 1993.

Abadi, et al.; "Synthesis and Cyclooxygenase Inhibitory Properties of Novel (+) 2-(6-Methoxy-2naphthyl) propanoic acid (naproxen) derivatives"; vol. 334, No. 3, pp. 104-106; 2001.

Giordano, et al. "A Stereoconvergent Strategy for the Synthesis of Enantiomercialy Pure (R)-(-) and (S)-(+)-2-(6-Methoxy-2-Naphthyl)-Pfopanoic Acid (Naproxen)"; vol. 45, No. 13; pp. 4243-4252; 1989.

Yutaka Kawashima, et al.; "Synthesis and Pharmacological Evaluation of (Nitrooxy) alkyl Apovincaminates"; J. Med. Chem, 1993, vol. 36, No. 7, pp. 815-819.

Toshihisa Ogawa, et al.; "Synthesis and Antihypertensive Activities of New 1,4-Dihydropyridine Derivatives Containing N itrooxyalkylester M oieties a the 3-and 5-Positions"; Chem. Pharm. Bull. 1993, vol. 41, No. 6, pp. 1049-1054.

Claudio Giordano, et al.; A Stereoconvergent Strategy For the Synthesis of Enamtiomerically Pure (R)-(-) and (S)-(+)-2-(6-Methoxy-2-Naphthyl)-Propanoic Acid (Naproxen); 1989, vol. 45, No. 13, pp. 4243-4252.

Ashraf H. Abadi, et al.; "Synthesis and Cyclooxygenase Inhibitory P roperties of Novel (+) 2-(6-Methoxy-2-napphthyl)propanoic Acid (Naproxene) Derivatives" 2001, pp. 104-106.

Kawaken Fine Chem. Co., Ltd.; Derwent Publications Ltd.; Section Ch, Week 199347, Oct. 26, 1993.

* cited by examiner

*Primary Examiner*—Fiona T. Powers
(74) *Attorney, Agent, or Firm*—Arent Fox LLP

(57) ABSTRACT

The present invention refers to a process for preparing a compound of general formula (A), as reported in the description, wherein R is a radical of naproxen or bromonaproxen and $R_1$–$R_{12}$ are hydrogen or alkyl groups, m, n, o, q, r and s are each independently an integer from 0 to 6, and p is 0 or 1, and and X is O, S, SO, $SO_2$, $NR_{13}$ or PR13 or an aryl, heteroaryl group, said process comprising reacting a compound of formula (B)

$$R\text{—}COOZ \qquad (B)$$

wherein R is as defined above and Z is hydrogen or a cation selected from: Li+, Na+, K+, Ca++, Mg++, tetralkylammonium, tetralkylphosphonium, with a compound of formula (C), as reported in the description, wherein R1–R12 and m, n, o, p, q, r, s are as defined above and Y is a suitable leaving group.

9 Claims, No Drawings

PROCESS FOR PREPARING NITROOXYDERIVATIVES OF NAPROXEN

CROSS-REFERENCE TO RELATED APPLICATION

This application is a National Stage entry of International Application No. PCT/EP2003/008698, filed Aug. 6, 2003, the entire specification and claims of which are incorporated herewith by reference.

The present invention relates to a process for preparing nitrooxyalkylesters of naproxen (2-(S)-(6-methoxy-2-naphtyl)-propanoic acid) or bromonaproxen (2-(S)-(5-bromo-6-methoxy-2-naphtyl)-propanoic acid) (Tetrahedron 1989, Vol 45, pages 4243–4252).

It is well known in the prior art that the anti-inflammatory activity of (2-(S)-(6-methoxy-2-naphtyl)-propanoic acid) is due to the S enantiomer which is the product in the market (Naproxen).

WO 01/10814 discloses a process for preparing the nitroxybutylester of the 2-(S)-(6-methoxy-2-naphtyl)-propionic acid by reacting the (2-(S)-(6-methoxy-2-naphtyl)-propionyl chloride with 4-nitrooxybutan-1-ol in methylene chloride and in presence of potassium carbonate. The obtained ester has an enantiomeric excess (e.e.) higher than or equal to 97%. This method has the disadvantage that several by-products are formed, being in fact very difficult to obtain nitrooxyalkyl alcohols in pure form and 2-arylpropanoyl halides of high chemical and enantiomerical purity. Moreover, for example 4-nitrooxybutan-1-ol is stable only in solution and it cannot be isolated as a pure substance.

The present invention provides a new process for preparing nitrooxyalkylesters of naproxen or bromonaproxen having an enantiomeric excess as high as that of the starting naproxen or bromonaproxen wherein impurities and by-products are present in an essentially negligible amount. Therefore, starting from enantiomerically pure Naproxen, enantiomerically pure esters are obtained. This is of particular importance because: i) most of the nitrooxyalkyl esters of Naproxen are low melting point or liquid substances, consequently the e.e. of the obtained crude esters cannot be enhanced by conventional physical methods ii) the absence of functional groups, apart from the ester one, in the molecules under consideration makes the purification problematic.

Another advantage of the present invention is that the starting compounds are stable. The process of the present invention uses as starting material a salt of Naproxen and a nitrooxy alkyl derivative having a leaving group, as substituent, in the alkyl chain.

Naproxen salt is used as ammonium or alkaline metals salt. The sodium salt is chemically and enantiomerically stable and, and is commercially available instead of 2-(S)-(6-methoxy-2-naphtyl)-propanoyl chloride (Naproxen chloride),is not commercially available in large scale, is chemically unstable and easy to racemize.

Also the nitrooxy alkyl derivative are more stable in comparison to the corresponding nitrooxyalkyl alcohol. Therefore both reagents involved in the present process, are by far more stable in comparison to those reported in the prior art.

The observed high selectivity of the process was unexpected, because of the presence of two substituents on the nitrooxy alkyl derivative, the nitrooxy and the leaving group, which were expected to compete in the displacement reaction by the Naproxen salt with concomitant loss of process selectivity. Another advantage of the present invention is that the starting compounds are stable. The process of the present invention uses as starting material naproxen salt, instead of the acid chloride of the prior art process, in particular the sodium salt which is a stable and commercially available product.

Bromonaproxen nitroxooyakylesters are per se biologically active and can be converted into the corresponding naproxen esters by conventional method.

The present invention relates to a process for preparing a compound of general formula (A)

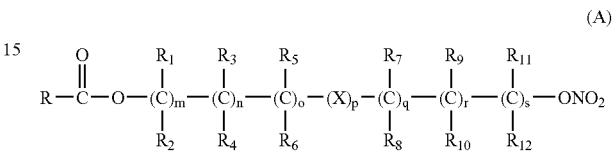

wherein:
R is

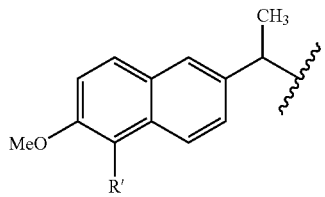

in which R' is a hydrogen atom or Br $R_1$–$R_{12}$ are the same or different and independently are hydrogen, straight or branched $C_1$–$C_6$ alkyl, optionally substituted with aryl;

m, n, o, q, r and s are each independently an integer from 0 to 6, and p is 0 or 1, and X is O, S, SO, $SO_2$, $NR_{13}$ or $PR_{13}$, in which $R_{13}$ is hydrogen, $C_1$–$C_6$ alkyl, or X is selected from the group consisting of:

cycloalkylene with 5 to 7 carbon atoms into cycloalkylene ring, the ring being eventually substituted with side chains T, wherein T is straight or branched alkyl with from 1 to 10 carbon atoms, preferably $CH_3$;

arylene, optionally substituted with one or more halogen atoms, straight or branched alkyl groups containing from 1 to 4 carbon atoms, or a straight or branched $C_1$–$C_3$ perfluoroalkyl;

a 5 or 6 member saturated, unsaturated, or aromatic heterocyclic ring selected from

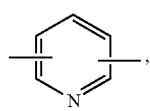
(X1)

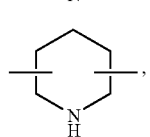
(X2)

-continued

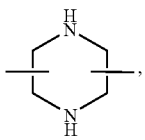
(X3)

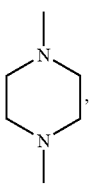
(X4)

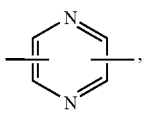
(X5)

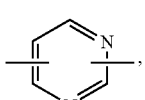
(X6)

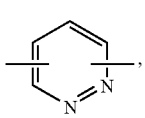
(X7)

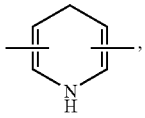
(X8)

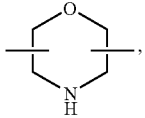
(X9)

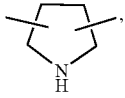
(X10)

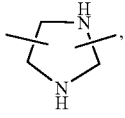
(X11)

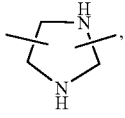
(X12)

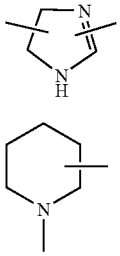
(X13)

wherein the bonds, when they have an undefined position, are intended to be in any possible position in the ring; said process comprising i) reacting a compound of formula (B)

R—COOZ (B)

wherein R is as above defined and Z is hydrogen or a cation selected from:

Li+, Na+, K+, Ca++, Mg++, ammonium, trialkylammonium tetralkylammonium and tetralkylphosphonium;

with a compound of the following formula (C)

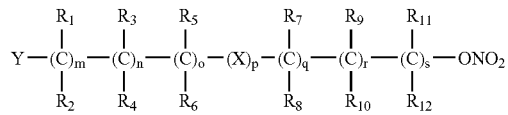
(C)

wherein $R_1$–$R_{12}$ and m, n, o, p, q, r, s are as defined above and Y is selected from a halogen atom —$BF_4$, —$SbF_6$, $FSO_3$—, $ClO_4$—, $R_ASO_3$—, in which $R_A$ is a straight or branched $C_1$–$C_6$ alkyl, optionally substituted with one or more halogen atoms, or a $C_1$–$C_6$ alkylaryl;

$R_BCOO^-$, wherein $R_B$ is straight or branched $C_1$–$C_6$ alkyl, aryl, optionally substituted with one or more halogen atoms or $NO_2$ groups, $C_4$–$C_{10}$ heteroaryl and containing one or more heteroatoms, which are the same or different, selected from nitrogen, oxygen sulfur or phosphorus;

aryloxy optionally substituted with one or more halogen atoms or $NO_2$ groups, or heteroaryloxy and ii) optionally converting a compound of formula (A) wherein R' is Br into a compound of formula (A) wherein R' is hydrogen.

Preferably the present invention relates to a process for preparing a compound of formula A as above defined wherein: the substituents $R_1$–$R_{12}$ are the same or different and independently are hydrogen or straight or branched $C_1$–$C_3$ alkyl, m, n, o, p, q, r and s are as defined above, X is O, S or

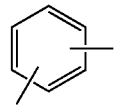

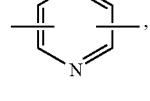
(X1)

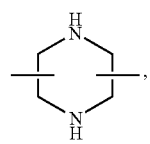
(X2)

(X3)

-continued (X4)

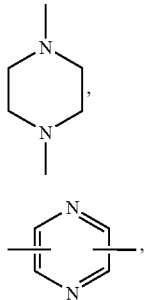

(X5)

Most preferably the invention relates to process for preparing a compound of formula A according to claim 1 or 2 wherein $R_1$–$R_4$ and $R_7$–$R_{10}$ are hydrogens, m, n, q, r, are 1, o and s are 0, p is 0 or 1, and X is O or S.

In the compounds of formula (C), preferably Y is selected from the group consisting of Br, Cl, I, —$BF_4$, $ClO_4^-$, —$SbF_6$, $FSO_3$—, $CF_3SO_3$—, $C_2F_5SO_3$—, $C_3F_7SO_3$—, $C_4F_9SO_3$—, p-$CH_3C_6H_4SO_3$—.

The reaction between a compound of formula (B) and a compound of formula (C) may be carried out in an organic solvent selected from acetone, tetrahydrofurane, dimethylformamide, N-methylpyrrolidone, sulfolane and acetonitrile.

Alternatively the reaction may be carried out in a biphasic system comprising an aprotic dipolar solvent selected from toluene, chlorobenzene, nitrobenzene, tert-butyl-methylether and a water solution wherein the organic solution contains (C) and the water solution contain an alkaline metal salt of (B), in presence of a phase transfer catalyst such as onium salts, for example tetralkylammonium and tetralkylphosphonium salts.

The reaction is carried out at a temperature ranging from 0° C. to 100° C. and at a (B)/(C) molar ratio of 2–0.5.

The carboxylic acid salt may be prepared separately or can be generated "in situ", for example performing the reaction between (B) and (C) in the presence of a stoichiometric amount of a tertiary amine, or employing an amount in excess of said amine.

The compounds of formula (C),may be prepared by nitrating compounds of formula (D) reported here below, with nitrating agents selected for example, sulfonitric mixture and the like:

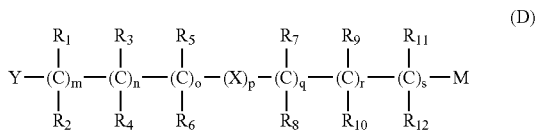

(D)

wherein M is OH, and

Y, X, m, n, o, p, q, r, s and $R_1R_{12}$, have the meanings mentioned above.

Alternatively the compounds of formula (C) may be obtained by reacting a compound of formula (E) with nitrating agents selected for example from alkaline metal nitrates, quaternary ammonium nitrates, quaternary phosphonium salts and $AgNO_3$, $Zn(NO)_2 \cdot 6H_2O$:

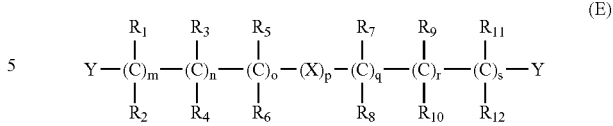

(E)

wherein:

Y, X, m, n, o, p, q, r, s and $R_1$–$R_{12}$, have the meanings mentioned above.

Alternatively the compounds of formula (C) may be obtained by reacting a compound of formula (F)

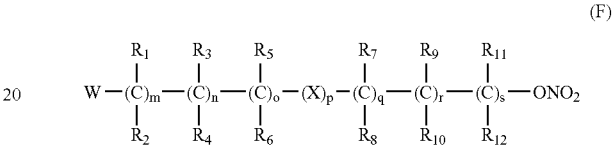

(F)

wherein W is OH or halogen, with a compound selected from alkyl and aryl sulfonylchloride, trifluoromethansulfonic acid anhydride, when W is OH or $AgSbF_6$, $AgBF_4$, $AgClO_4$, $CF_3SO_3Ag$, $AgSO_3CH_3$, $CH_3C_6H_4SO_3Ag$ when W is halogen.

Nitration of compound (D) was performed in an organic solvent, generally in a solvent selected from acetone, tetrahydrofurane, dimethylformamide, N-methylpyrrolidone, sulfolane, acetonitrile, methylene chloride etc., with nitrating agents selected from transition metal salts or, when M is OH, with nitrating systems based on nitric acid, such as the sulfonitric mixture.

The (D)/nitrating agent molar ratio is of from 2 to 0.5, in particular of 1.5 to 0.5 and the nitration is carried at a temperature ranging from 0° C. to 100° C., preferably from 15° C. to 80° C.

The reaction product (C) may be isolated or its solution can be employed as such for the reaction with substrate (B) to give (A).

Nitration of compound (E) may be carried out in an organic solvent, generally in a solvent selected from acetone, tetrahydrofurane, dimethylformamide, N-methylpyrrolidone, sulfolane, acetonitrile, methylene chloride etc., with nucleophilic nitrating agents such as alkaline metal nitrates, onium salt nitrates, for example tetraalkylammonium, tetraalkyl-phosphonium or trialkylammonium nitrate and so on.

The reaction is carried out at a temperature of from 0° C. to 100° C., in particular of 15° C. to 80° C. and at a molar ratio (E)/nitrating agent of from 20 to 2, preferably of 8 to 1.

The reaction product (C) may be isolated or its solution can be employed such as in the reaction with substrate (B) to give (A).

The reaction for obtaining compound (C) from (F) may be carried out in an organic solvent, generally selected from the group consisting of acetone, tetrahydrofurane, dimethylformamide, N-methylpyrrolidone, sulfolane, acetonitrile, methylene chloride and the like, with a transition metals salts selected from those of silver, zinc, mercury or, when W is OH, the reaction was performed with an acid chloride such as methanesulfonyl chloride etc., or with a suitable anhydride such as trifluoro-methanesulfonic anhydride.

The reaction was performed at a temperature ranging from −20° C. to 100° C., in particular from −20° to 60° C. at a molar ratio compound (F)/reagent of from 2 to 0.5, preferably of 1.5 to 0.5.

The reaction product (C) may be isolated or its solution can be employed as such in the reaction with substrate (B) to give (A).

EXAMPLES

Preparation of 4-nitrooxybutyl bromide According to Chem. Pharm. Bull., 1993,41,1040

Nitric acid (90%, 0.8 mol) was dropped under stirring in sulfuric acid maintained at 0° C. (0.8 mol) and the mixture was then stirred at 0° C. for 80 minutes. In the solution thus obtained and maintained at 0° C., under stirring 4-bromobutanol was dropped (0.4 mol) and the mixture was stirred again for additional 210 minutes at the same temperature. The solution was then poured in a water-ice mixture and extracted twice with diethyl ether. The ether extracts were combined together and washed with a sodium bicarbonate saturated solution. The solvent was evaporated off under vacuum to give a yellow oil (yield: 84.8%).

Example 1

Preparation of 4-nitrooxybutyl p-toluenesulfonate

To a solution of 4-bromobutanol (5.0 g, 33 mmol) in pyridine (50 ml) kept at 0° C., under stirring and under nitrogen atmosphere tosyl chloride (6.8 g, 36 mmol) was added. The resulting solution was kept under stirring for further 20 minutes and then stored overnight at −18° C. The reaction mixture was poured in a water/ice mixture (about 400 ml) and extracted with ethyl ether (500 ml). The organic phase was washed with 6N hydrochloric acid (500 ml) and dried on sodium sulfate. Evaporation of the solvent under vacuum, provided an oily residue (7 g). To a solution of the oily residue (7 g, 23 mmol) in acetonitrile (50 ml), kept under stirring and under nitrogen at room temperature, silver nitrate (7.8 g, 46 mmol) was added. After nearly 15 minutes, the formation of a yellow, insoluble product was observed. The heterogeneous mixture was kept under stirring overnight. The insoluble was removed by filtration and the solution was poured in water (200 ml) and extracted with ethyl ether (2×250 ml). The combined organic extracts were dried over sodium sulfate. Evaporation of the solvent under vacuum afforded an oily residue (5 g).

Chromatography of the residue on silica gel (100 g), with hexane/ethyl ether mixture as eluent, gives the title product (3 g), m.p. 38–40° C. and a purity, determined by HPLC, higher than 98%,.

FTIR (solid KBr, cm-1): 2966, 1626, 1355, 1281, 1177, 1097, 959, 876, 815, 663, 553.

300 MHz 1H NMR (CDCl3) delta 1.77 (m, 4H); 2.35 (s, 3H); 4.06 (m, 2H); 4.38 (m, 2H); 7.36 (2H); 7.7 (2H).

Example 2

Synthesis 2-(S)-(6-methoxy-2-naphthyl)propanoic acid, 4-(nitrooxy)butyl ester

KHCO₃ (5.22 g, 52 mmol) was added under nitrogen to a solution of 2-(S)-(6-methoxy-2-naphthyl)propanoic acid (Naproxen) (99 e.e. determined by chiral HPLC) (10.0 g, 43 mmol) in DMF (200 ml).

The heterogeneous mixture was heated up to 50–60° C. and kept at this temperature under nitrogen and under magnetic stirring for 90 min. The reaction mixture was allowed to cool down to room temperature. Potassium iodide (2.14 g, 12.9 mmol) and 4-bromobutylnitrate (14.48 g 73 mmol) were added to the above mixture, and the reaction mixture was stirred at room temperature under nitrogen for 25 h. Water (200 ml) was added dropwise in 5 min. to the reaction mixture. The mixture was extracted with t-BuOMe (200 ml), the organic phase was washed with NaCl 10% aqueous solution (2×200 ml) and was dried over Na₂SO₄ Evaporation of the solvent in vacuo provided an oily residue (17.3 g). Chromatography on silica gel (eluent hexanes/ethyl acetate) of the residue provided 2-(S)-(6-methoxy-2-naphthyl)propanoic acid,4-(nitrooxy)butyl ester as an yellow oily compound (10.8 g, 73% yield, e.e., determined by HPLC, higher than 99%).

The product was identified by comparison with an authentic sample.

Example 3

Synthesis 2-(S)-(6-methoxy-2-naphthyl)propanoic acid, 4-(nitrooxy)butyl ester

KHCO₃ (5.22 g, 52 mmol) was added under nitrogen to a solution of 2-(S)-(6-methoxy-2-naphthyl)propanoic acid (Naproxen) (99 e.e. determined by chiral HPLC) (10.0 g, 43 mmol) in DMF (200 ml).

The heterogeneous mixture was heated up to 50–60° C. and kept at this temperature under nitrogen and under magnetic stirring for 90 min. The reaction mixture was allowed to cool down to room temperature. 4-(nitrooxy)butyl-4-methylbenzenesulphonate (21.1 g 73 mmol) was added to the above mixture, and the reaction mixture was stirred at room temperature under nitrogen for 25 h. Usual aqueos work up followed by chromatography on silica gel (eluent hexanes/ethyl acetate) of the reaction crude provided 2-(S)-(6-methoxy-2-naphthyl)propanoic acid,4-(nitrooxy)butyl ester (10.4 g, 70% yield, e.e., determined by HPLC, higher than 99%).

Example 4

Synthesis 2-(S)-(+)-(5-bromo-6-methoxy-2-naphthyl)propanoic acid, 4-(nitrooxy)butyl ester A mixture of triethylamine (5.25 g, 52 mmol), of 2-(S)-(5-bromo-6-methoxy-2-naphthyl)propanoic acid (Bromo-Naproxen) (13.3 g, 43 mmol); e.e.99%) and of 4-bromobutylnitrate (43 mmol) in DMF (120 ml) was stirred under nitrogen for 2 days at 25° C.

Removal of DMF under vacuum followed by usual aqueous work up provided the reaction crude. Chromatography on silica gel (eluent hexanes/ethyl acetate) of the residue provided pure 2-(S)-(5-bromo-6-methoxy-2-naphthyl)propanoic acid,(nitrooxy)butyl ester (11.9 g; 65% yield; e.e., determined by HPLC, higher than 99%).

The product was identified by spectroscopic methods.

The invention claimed is:

1. A process for preparing a compound of general formula (A)

(A)

$$R-\underset{\|}{C}-O-(C)_m-(C)_n-(C)_o-(X)_p-(C)_q-(C)_r-(C)_s-ONO_2$$

with substituents $R_1, R_2$ on $(C)_m$; $R_3, R_4$ on $(C)_n$; $R_5, R_6$ on $(C)_o$; $R_7, R_8$ on $(C)_q$; $R_9, R_{10}$ on $(C)_r$; $R_{11}, R_{12}$ on $(C)_s$.

wherein:
R is

[Structure: 2-methoxynaphthalene with CH(CH$_3$)- attachment point at the 6-position and R' substituent]

in which R' is a hydrogen atom or Br $R_1$–$R_{12}$ are the same or different and independently are hydrogen, straight or branched $C_1$–$C_6$ alkyl, optionally substituted with aryl;

m, n, o, q, r and s are each independently an integer from 0 to 6, and p is 0 or 1, and X is O, S, SO, SO$_2$, NR$_{13}$ or PR$_{13}$, in which R$_{13}$ is hydrogen, $C_1$–$C_6$ alkyl, or X is selected from the group consisting of:

cycloalkylene with 5 to 7 carbon atoms into cycloalkylene ring, the ring being eventually substituted with side chains T, wherein T is straight or branched alkyl with from 1 to 10 carbon atoms;

arylene, optionally substituted with one or more halogen atoms, straight or branched alkyl groups containing from 1 to 4 carbon atoms, or a straight or branched $C_1$–$C_3$ perfluoroalkyl;

a 5 or 6 member saturated, unsaturated, or aromatic heterocyclic ring selected from (X1) pyridine
(X2) piperidine
(X3) piperazine
(X4) N-methylpiperazine
(X5) pyrazine
(X6) pyrimidine
(X7) pyridazine
(X8) dihydropyridine (NH)
(X9) morpholine
(X10) pyrrolidine
(X11) imidazolidine
(X12) imidazoline
(X13) N-methylpiperidine said process comprising:
i) reacting a compound of formula (B)

R—COOZ    (B)

wherein R is as above defined and Z is hydrogen or a cation selected from Li+, Na+, Ca++, Mg++, tetralkylammonium, tetralkylphosphonium, with a compound of formula (C)

(C)

$$Y-(C)_m-(C)_n-(C)_o-(X)_p-(C)_q-(C)_r-(C)_s-ONO_2$$

with substituents $R_1, R_2$ on $(C)_m$; $R_3, R_4$ on $(C)_n$; $R_5, R_6$ on $(C)_o$; $R_7, R_8$ on $(C)_q$; $R_9, R_{10}$ on $(C)_r$; $R_{11}, R_{12}$ on $(C)_s$.

wherein $R_1$–$R_{12}$ and m, n, o, p, q, r, s are as defined above and

Y is selected from
a halogen atom

—BF$_4$, —SbF$_6$, FSO$_3$—, R$_A$SO$_3$—, in which R$_A$ is a straight or branched C$_1$–C$_6$ alkyl, optionally substituted with one or more halogen atoms, or a C1–C6 alkylaryl;

R$_B$COO$^-$, wherein R$_B$ is straight or branched C$_1$–C$_6$ alkyl, aryl, optionally substituted with one or more halogen atoms or NO$_2$ groups, C$_4$–C$_{10}$ heteroaryl and containing one or more heteroatoms, which are the same or different, selected from nitrogen, oxygen sulfur or phosphorus;

aryloxy optionally substituted with one or more halogen atoms or NO$_2$ groups, or heteroaryloxy and ii) optionally converting a compound of formula (A) wherein R' is Br in a compound of formula (A) wherein R' is hydrogen.

2. A process for preparing a compound of formula A according to claim 1 wherein:

the substituents R$_1$–R$_{12}$ are the same or different and independently are hydrogen or straight or branched C$_1$–C$_3$ alkyl, m, n, o, p, q, r and s are as defined above, X is O, S or

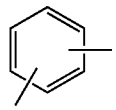
(X1)

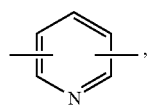
(X2)

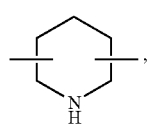
(X3)

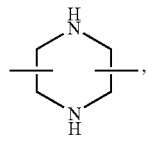
(X4)

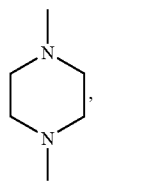

-continued

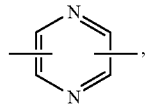
(X5)

3. A process for preparing a compound of formula A according to claim 1 wherein R$_1$–R$_4$ and R$_7$–R$_{10}$ are hydrogens, m, n, q, r, are 1, o and s are 0, p is 0 or 1, and X is O or S.

4. A process for preparing a compound of formula A according to claim 1 wherein Y is selected from the group consisting of Br, Cl, I, —BF$_4$, —SbF$_6$, FSO$_3$—, ClO$_4$, CF$_3$SO$_3$—, C$_2$F$_5$SO$_3$—, C$_3$F$_7$SO$_3$—, C$_4$F$_9$SO$_3$—, p-CH$_3$C$_6$H$_4$SO$_3$—.

5. A process for preparing a compound of formula A according to claim 1 wherein the reaction is performed in an organic solvent selected from acetone, tetrahydrofurane, dimethylformamide, N-methylpyrrolidone, sulfolane and acetonitrile.

6. A process for preparing a compound of formula A according to claim 1 wherein the reaction is performed in a biphasic system comprising an aprotic dipolar solvent selected from toluene, chlorobenzene, nitrobenzene, tert-butylmethylether and a water solution wherein the organic solution contains (C) and the water solution contain an alkaline metal salt of (B), in presence of a phase transfer catalyst.

7. A process for preparing a compound of formula A according to claim 1 wherein the reaction is performed at a temperature ranging from 0° C. to 100° C.

8. A process for preparing a compound of formula A according to claim 1 wherein the compounds of formula B and C are reacted at a (B)/(C) molar ratio of 2–0.5.

9. 2-(S)-(5-bromo-6-methoxy-2-naphthyl)propanoic acid, 4-(nitrooxy)butyl ester.

* * * * *